United States Patent [19]

Ripple et al.

[11] Patent Number: 4,566,466

[45] Date of Patent: Jan. 28, 1986

[54] SURGICAL INSTRUMENT

[76] Inventors: Dale B. Ripple, 1130 Singingbrook Dr., NW.; David W. Smith, 5685 Arlington Ave., NW., both of Massillon, Ohio 44646

[21] Appl. No.: 600,970

[22] Filed: Apr. 16, 1984

[51] Int. Cl.⁴ .............................................. A61B 5/10
[52] U.S. Cl. ................................... 128/781; 128/92 E
[58] Field of Search .............. 128/92 E, 92 A, 303 R, 128/781

[56] References Cited

U.S. PATENT DOCUMENTS

| | | | |
|---|---|---|---|
| D. 249,705 | 9/1978 | London | |
| 2,290,432 | 7/1942 | Neil | 33/174 |
| 3,486,505 | 12/1969 | Morrison | 128/303 R |
| 3,738,355 | 7/1973 | Salvatore | 128/2 |
| 4,033,043 | 7/1977 | Cunningham | 33/143 R |
| 4,440,168 | 4/1984 | Warren | 128/92 E |
| 4,450,834 | 5/1984 | Fischer | 128/92 A |

OTHER PUBLICATIONS

Whiteside Ortholoc Total Knee System (Dow Corning Wright, 1983).

Primary Examiner—Peter D. Rosenberg
Attorney, Agent, or Firm—Michael Sand Co.,

[57] ABSTRACT

An improved surgical instrument for performing an anterior cervical interbody arthrodesis includes a template head and a handle connected by a stem. The head has a predetermined thickness and a plurality of depth indicating lines marked on one of the surfaces thereof. The handle is grasped by a surgeon and the template head is inserted into a space previously occupied by an intervertebrated disc after removal of the disc by the surgeon. The depth of penetration of the head into the space is determined from the depth indication lines and the width of the space determined from the thickness of the template head. The head of the device is layed on an exposed iliac crest of the patient to provide a template for removing the desired thickness of bone graft. The removed bone graft is layed on the flat surface of the head and sized in thickness by the indication lines in relationship to the depth of the space previously measured the indication lines on the head. This produces an accurately sized bone graft in both length and thickness which is then placed in the space between the end plates of spaced vertebral bodies to be fused thereby.

12 Claims, 12 Drawing Figures

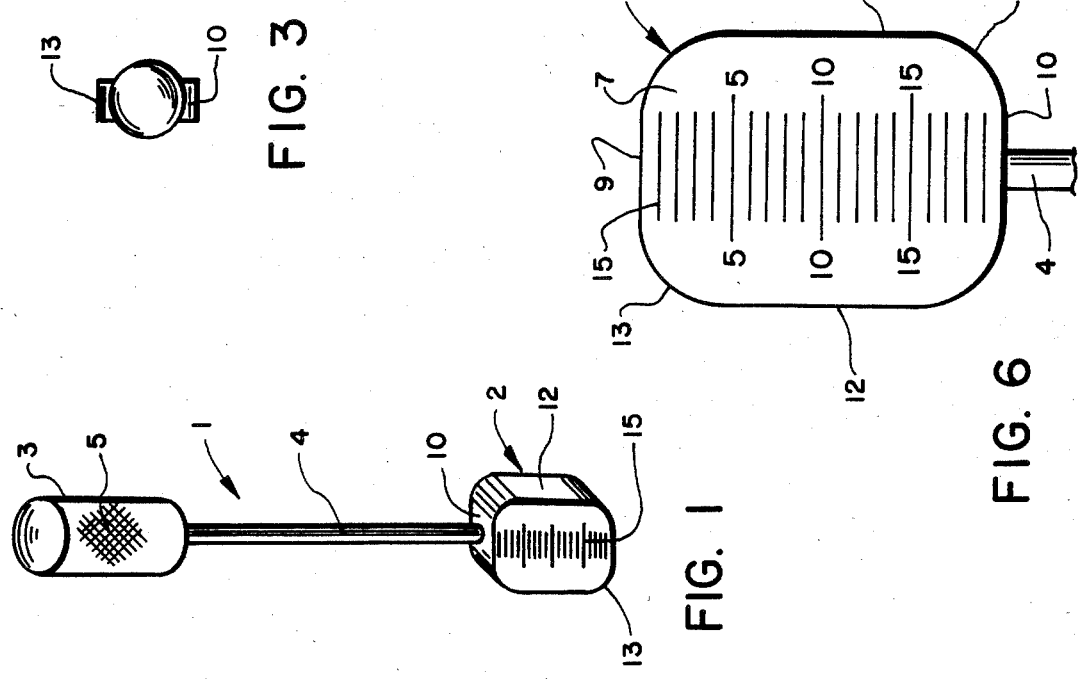

SURGICAL INSTRUMENT

TECHNICAL FIELD

The invention relates to surgical instruments and in particular to an instrument for performing an anterior cervical interbody arthrodesis. More particularly, the invention relates to such an instrument which enables an accurately sized bone graft to be removed from a patient's hip bone to match the space formed between vertebral bodies by a surgeon for fusing the bodies together.

BACKGROUND ART

A common surgical procedure performed by many surgeons involves the placement of a bone graft, usually secured from the iliac crest or hip bone of a patient, between vertebral bodies after the intervertebral disc material has been removed to eliminate pain and suffering of the patient caused by a diseased or injured disc. One type of instrument used for a similar procedure is shown in U.S. Pat. No. 3,486,505.

The existing surgical method is for a sling to be applied around the patient's neck to distract or separate adjacent vertebral bodies after which an anterior surgical approach is made in the neck usually off to the right side directly over the sternocleiodmastic muscle. The plane of disection is just anterior to the sternocleiodmastoid muscle through the retropharyngeal space whereby the anterior cervical spine is ordinarily reached without great difficulty and certainly without endangering underlying structures. After the level to be fused have been identified, the intervertebral disc material is removed with a knife blade and curette and pituitary rongeurs. These instruments remove the entire disc both nucleus pulposus and anulus fibrosus. A disc space spreader then is applied and the disection is continued with a right angled curette down to the posterior longitudinal ligament and out over both foramina. Retractors then are removed and a drill is used to decorticate the end plates of the vertebral bodies that are to be fused. Once this disection has been completed a bone graft is taken from an exposed iliac crest of the patient and inserted into the formed space between the vertebral bodies earlier occupied by the intervertebral discs.

Heretofore, the size of the bone graft that was removed from the iliac crest was by sight and trial and error with respect to the size of the space formed between the vertebral bodies. Usually the bone graft was cut to a larger size than believed necessary and then sized by trial and error until it fit into the formed space. This required additional time on behalf of the surgeon and could result in an improperly sized graft being placed into the space between the vertebral bodies.

Therefore, the need has existed for a surgical instrument which enables a surgeon to accurately determine the size of bone graft to be removed from the iliac crest for subsequent placement in the space formed between the vertebral bodies to be fused.

DISCLOSURE OF THE INVENTION

Objectives of the invention include providing an improved orthopedic surgical instrument for use in the procedure of anterior cervical interbody arthrodesis which enables an accurately sized bone graft, in both length and width, to be removed from the exposed iliac crest of the patient and matched to a space between an adjacent pair of vertebral bodies previously occupied by the intervertebral disc after removal by the surgeon. Another objective is to provide such an instrument which is of an extremely simple design which includes a template head that is adapted to be inserted into the space between the vertebral bodies; in which a plurality of depth indicating lines are marked on the template head enabling the physician to accurately determine the depth of penetration of the head into the space; and in which the template head may vary in thickness enabling the physician to choose the proper thickness of head which fits into the formed space.

Another objective is to provide such a surgical instrument which is adapted to be layed on the iliac crest and used as a template for removing the desired thickness of bone graft from the crest and in which the graft then is layed on the depth indicating surface of the template head for sizing the removed bone graft to the desired length prior to placing the graft into the space between the vertebral bodies. Still another objective is to provide such an instrument which can be formed of stainless steel enabling it to be maintained in an anticeptic and sanitary condition by usual procedures used for other surgical instruments; in which the instrument has a handle that is easily grasped by a surgeon for inserting the template head into the space between the vertebral bodies; and in which the template head of the instrument preferably is formed in a range of sizes as to the thickness thereof enabling the surgeon to select the desired thickness head to measure the width of the space between the vertebral bodies for subsequent use as a template on the iliac crest.

A further objective is to provide a device which eliminates difficulties existing with prior surgical instruments used for such a surgical procedure, which is sturdy, durable and sanitary in use, which is easily used with a minimum of training, and which saves considerable time during the surgical operation while providing an extremely accurately sized bone graft for placement between distracted vertebral bodies.

These objectives and advantages are obtained by the improved surgical device of the present invention, the general nature of which may be stated as a device for sizing a graft to be removed from the iliac crest for insertion into a space between distracted vertebral bodies, said device including; a template head having a pair of spaced parallel flat surfaces separated a predetermined distance by an inner and outer end surface and a pair of side surfaces; a handle for grasping by a surgeon; a stem projecting outwardly from the inner end surface and extending between and connecting the template head and handle; and a plurality of depth indicating means formed on one of the flat surfaces of the template head for indicating distance from the outer end surface of said template head.

BRIEF DESCRIPTION OF THE DRAWINGS

FIG. 1 is a perspective view of the improved surgical instrument;

FIG. 2 is a plan view of the improved surgical instrument of FIG. 1;

FIG. 3 is a left-hand end view of the surgical instrument as shown in FIG. 2;

FIG. 4 is a right-hand end elevational view of the surgical instrument as shown in FIG. 2;

FIG. 5 is a side plan view of the improved surgical instrument;

FIG. 6 is an enlarged fragmentary plan view of the template head portion of the improved surgical instrument;

FIG. 7 is a fragmentary view of a plurality of the improved surgical instruments for forming a set thereof;

Similar numerals refer to similar parts throughout the drawings.

BEST MODE FOR CARRYING OUT THE INVENTION

Figure 8:
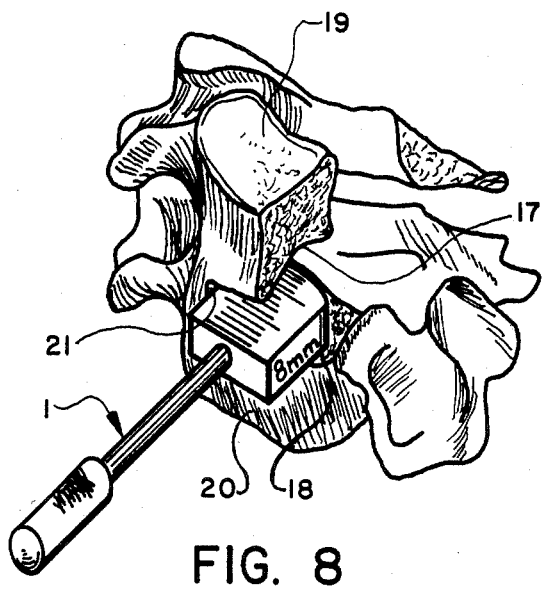
FIG. 8 is a diagrammatic perspective view showing the improved surgical instrument being inserted into a space previously occupied by an intervertebral disc between vertebral bodies.

The improved surgical instrument is indicated generally at 1, and is shown particularly in FIGS. 1–5. Instrument 1 which also may be referred to as a sizertemplate, includes a template head indicated generally at 2, which is connected to a handle 3 by a stem 4. Instrument 1 preferably is formed of stainless steel as are most surgical instruments, to provide a device which is extremely durable and can be maintained in a sanitary condition by usual sanitizing means and equipment.

Handle 3 is a cylindrical-shaped body having a knurled surface 5 enabling it to be easily gripped and manipulated by a surgeon even while wearing surgical gloves. Stem 4 is a cylindrical shaped rod which is inserted into complementary shaped holes formed in handle 3 and template head 2 and secured therein, preferably by soldering. Handle 3 may have other configurations than the cylindrical shape shown in the drawings, such as being a flat member or other configuration whereby it is easily gripped and manipulated by a surgeon.

In accordance with one of the features of the invention, template head 2 as shown particularly in FIG. 6, preferably is a solid body formed of stainless steel having a pair of spaced, parallel surfaces 7 and 8, outer and inner end surface 9 and 10, and a pair of spaced parallel side surfaces 11 and 12 which are connected to end surfaces 9 and 10 by rounded corners 13. A plurality of depth indicating lines 15 are engraved in surface 7 denoting the distance along surface 7 from outer end surface 9 toward inner end surface 10. Lines 15 preferably are spaced at one millimeter distance and extend generally in a transverse direction across surface 7. Intervals of five millimeters are generally engraved with the numeric indication providing a rapid and easy means for the surgeon to determine the depth of penetration of template head 2 into the space between vertebral bodies as described in greater detail below.

Preferably a plurality of surgical instruments 1 will be used as a set as shown in FIG. 7 for the surgical procedure. The only difference between the individual instruments of the set is the thickness of template head 2 or the height of surfaces 9–12. It has been found that a series of eight instruments ranging between 5 mm to 12 mm in thickness with each instrument being 1 mm thicker than the adjacent instrument has proved satisfactory for performing most of the intended operations. In the preferred embodiment instrument 1 has an overall length of 5.0 centimeters and template head 2 has a width of 1.5 centimeters and a length of 2.0 centimeters.

The manner of use of improved surgical instrument 1 is shown in FIGS. 8–12. The method utilized for instrument 1 is similar to the procedure fashioned after a technique commonly referred to as the Smith-Robinson technique set forth briefly in the background portion of the specification. An anterior surgical approach is made in the neck usually off to the right side directly over the sternocleiodmastic muscle. A disection is made just anterior to the sternocleiodmastoid muscle through the retropharyngeal space. Retractors then are applied directly interior to the interior longitudinal ligament and buried in the longus colli muscles. Once the level to be fused has been identified, usually by placing a needle adjacent the injured or diseased disc followed by an X-ray to show the exact position of the disc, the intervertebral disc material then is removed usually with a knife blade, curette and pituitary rongeurs. These are all well known devices and procedures enabling the entire disc to be removed, both nucleus pulposus and anulus fibrorus.

A drill having a bur is used to decorticate the end plates 17 and 18 of the spaced vertebral bodies 19 and 20 (FIG. 8) forming a space 21 therebetween heretofore occupied by the removed disc material. The size of space 21 is dependent upon the condition of the disc and of the surrounding vertebral bodies 19 and 20 and upon the patient's physical condition, age, etc.

Once this disection has been completed and the damaged disc material removed to form space 21, improved instrument 1 comes into play. The surgeon selects an instrument 1 from the series of instruments which he believes to have the template head thickness corresponding to the width of space 21. Template head 2 is inserted into space 21 as shown in FIG. 8 providing the surgeon with an immediate and accurate indication as to the width of space 21 by the particular thickness of the template head 2. Several instruments may have to be selected and tried before the correctly sized instrument is selected. For example, as shown in FIG. 8, the particular template head having a thickness of 8 mm fits snugly into space 21. The surgeon also has an immediate measurement of the depth of space 21 by the amount of penetration of template head 2 therein which is easily read from line 15.

Figure 9:
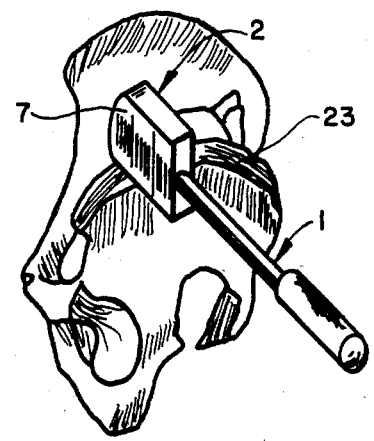
FIG. 9 is a diagrammatic perspective view showing the improved surgical instrument being placed on the iliac crest as a template for determining the size of bone graft to be removed therefrom.
Figure 10:
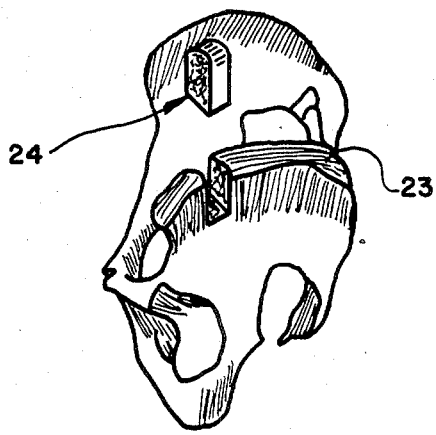
FIG. 10 is a diagrammatic perspective view showing the bone graft measured by the improved surgical instrument of FIG. 9 removed from the iliac crest.
Figure 11:
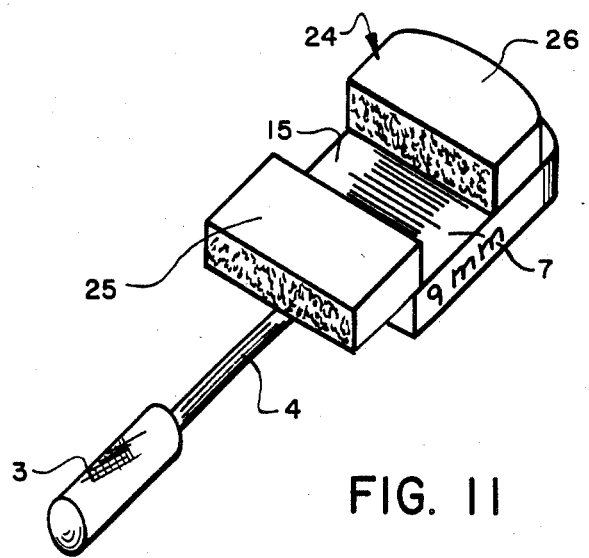
FIG. 11 is an enlarged diagrammatic perspective view showing the removed bone graft being sized by the template head to the desired length.

The surgeon then uses the particular sized instrument 1 which fitted into space 21, or may increase it by 1 mm, for securing the properly sized bone graft. The surgeon lays the edge of the selected instrument on the iliac crest 23 of the patient's hip as shown in FIG. 9, which indicates the required thickness of a bone graft 24 (FIG. 10) to be removed therefrom. The surgeon may mark the thickness of the bone graft on the iliac crest with a marking pen or similar instrument, after which the desired thickness bone graft 24 is removed, or he may use the flat surfaces 7 and 8 of the template head 2 as guides for a surgical saw in removing graft 24. As shown in FIG. 10, bone graft 24 is removed from iliac crest 23 and has a width corresponding to that of template head 2 of the selected instrument. The length of bone graft 24 then is accurately determined by laying the bone graft on flat surface 7 of template head 2 containing depth lines 15 (FIG. 11). The surgeon then removes a predetermined amount of end section 25 from graft 24 so that the remaining bone graft portion 26 has the required length previously determined by the depth of penetration of instrument 1 into space 21 as shown in FIG. 8. Preferably bone graft portion 26 is cut one millimeter shorter than the length previously measured by template head 2 to prevent the inserted bone graft from penetrating too far into space 21 and contacting the spinal cord.

Figure 12:
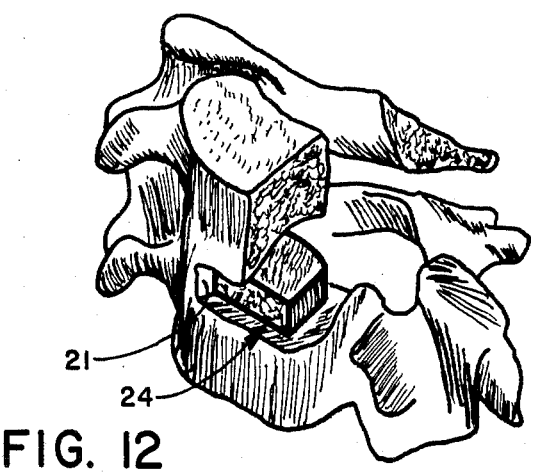
FIG. 12 is a diagrammatic perspective view showing the sized bone graft placed in the space between the intervertebral bodies.

Bone graft 26 then is inserted by the surgeon into space 21 as shown in FIG. 12 knowing that it has the proper size, thickness and length determined by instrument 1. Graft 26 preferably is sized approximately 1 mm thicker than the particular instrument 1 that was fitted within space 21 in the procedure of FIG. 8 enabling the graft to be securely wedged into position between the vertebral bodies.

Accordingly improved surgical instrument 1 provides for the expeditious sizing of a graft to be removed from a patient's hip for placement in the space between a pair of vertebral bodies, which enables the surgeon to measure the depth that the graft is to be inserted into this space in a convenient manner, as well as determine the shape of the graft once removed from the patient's hip before inserting it into the space, and which functions as a cutting template when removing the graft from the patient's hip bone. This improved surgical instrument also removes most of the guess work heretofore used for such surgical procedures, eliminates putting the wrong size graft into the space between the vertebral bodies and causing problems at this level of surgery; and which cuts time off the surgical procedure.

Accordingly, the improved surgical instrument is simplified, provides an effective, safe, inexpensive, and efficient device which achieves all the enumerated objectives, provides for eliminating difficulties encountered with prior devices, and solves problems and obtains new results in the art.

In the foregoing description, certain terms have been used for brevity, clearness and understanding; but no unnecessary limitations are to be implied therefrom beyond the requirements of the prior art, because such terms are used for descriptive purposes and are intended to be broadly construed.

Moreover, the description and illustration of the invention is by way of example, and the scope of the invention is not limited to the exact details shown or described.

Having now described the features, discoveries and principles of the invention, the manner in which the improved surgical instrument is constructed and used, the characteristics of the construction, and the advantageous, new and useful results obtained; the new and useful structures, devices, elements, arrangements, parts, and combinations, are set forth in the appended claims.

What is claimed is:

1. A set of surgical instruments for sizing a graft to be removed from the iliac crest for insertion into a space between distracted vertebral bodies, each of said instruments including, a template head and handle means for inserting the head into the the space formed between the distracted vertebral bodies, said template head having a generally rectangular configuration formed by a pair of spaced parallel flat surfaces separated a predetermined distance by a generally flat planar outer end surface, an inner end surface, and a pair of flat planar side surfaces connected to the outer end surface by rounded corners to provide a desired thickness for each template head for determining the width of the space between the vertebral bodies with the thickness of the individual template heads varying in thickness with respect to each other to provide a range of template head thicknesses.

2. The set of surgical instruments defined in claim 1 in which depth indicating means is formed on at least one of the flat surfaces of each of the template heads for indicating distance from the planar outer end surface of said template head to indicate the depth of penetration of the head into the space between the vertebral bodies.

3. The set of surgical instruments defined in claim 1 in which the depth indicating means is a series of spaced parallel lines formed on the template head and extending parallel to the outer end surface of the head.

4. The set surgical instruments defined in claim 3 in which the lines are recessed in the template head by engraving.

5. The set of surgical instruments defined in claim 4 in which the depth indicating lines are spaced in at 1 mm intervals.

6. The set of surgical instruments defined in claim 1 in which the template head has a width of approximately 1.5 cm and a length of approximately 2 cm.

7. The set of surgical instruments defined in claim 1 in which the template heads vary in thickness from 5 mm to 12 mm.

8. The set of surgical instruments defined in claim 1 in which the overall length of each instrument is approximately 5 cm.

9. The set of surgical instruments defined in claim 1 in which the handle means is a cylindrical-shaped member having a knurled outer surface; and in which said handle member is connected to the head by a cylindrical rod.

10. The set of surgical instruments defined in claim 1 in which each template head varies in thickness approximately 1 mm from the adjacent sized head in the set of instruments.

11. The set of surgical instruments defined in claim 10 in which the set includes eight template heads ranging in thickness from 5 mm to 12 mm.

12. The set of surgical instruments defined in claim 11 in which the template heads are solid bodies of stainless steel.

* * * * *